United States Patent [19]

Chang

[11] Patent Number: 5,514,776
[45] Date of Patent: May 7, 1996

[54] PEPTIDES REPRESENTING ANTIGENIC EPITOPES OF DOG IGE PRESENT ON B CELL BUT NOT BASOPHIL SURFACE

[75] Inventor: Tse W. Chang, Houston, Tex.

[73] Assignee: Tanox Biosystems, Inc., Houston, Tex.

[21] Appl. No.: 326,767

[22] Filed: Oct. 20, 1994

Related U.S. Application Data

[63] Continuation-in-part of Ser. No. 137,253, Oct. 14, 1993, which is a continuation-in-part of Ser. No. 90,527, Jul. 9, 1993, Pat. No. 5,342,924, which is a continuation-in-part of Ser. No. 973,321, Oct. 29, 1992, Pat. No. 5,254,671, which is a continuation-in-part of Ser. No. 515,604, Apr. 27, 1990, Pat. No. 5,274,075, which is a continuation-in-part of Ser. No. 468,766, Jan. 23, 1990, Pat. No. 5,260,416, which is a continuation-in-part of Ser. No. 369,625, Jun. 21, 1989, which is a continuation-in-part of Ser. No. 272,243, Nov. 16, 1988, Pat. No. 5,091,313, which is a continuation-in-part of Ser. No. 229,178, Aug. 5, 1988, abandoned, which is a continuation-in-part of Ser. No. 226,421, Jul. 29, 1988, which is a continuation-in-part of Ser. No. 140,036, Dec. 31, 1987, abandoned.

[51] Int. Cl.⁶ ............... C07K 16/00; C07K 14/00; C12N 15/13

[52] U.S. Cl. .............. 530/300; 435/5; 530/387.1; 536/23.53

[58] Field of Search ............... 435/659.1, 252.3, 435/320.1; 514/19, 18, 17, 16, 15, 14, 13, 12; 500/387.1, 300, 350, 324, 325, 326, 327, 328, 329, 330; 526/23.53, 24.53

[56] References Cited

U.S. PATENT DOCUMENTS

| | | | |
|---|---|---|---|
| 5,089,603 | 2/1992 | Chang et al. | 530/387 |
| 5,091,313 | 2/1992 | Chang | 435/240.27 |

*Primary Examiner*—Donald E. Adams
*Attorney, Agent, or Firm*—Eric P. Mirabel

[57] ABSTRACT

Antigenic epitopes associated with the extracellular segment of the domain which anchors dog immunoglobulin-ε to the B cell membrane are disclosed. The epitopes are present on dog IgE-bearing B cells but not basophils or the secreted, soluble form of dog IgE. The peptides representing the epitopes associated with the anchor domain of dog IgE can be used to generate antibodies against these regions.

1 Claim, No Drawings

PEPTIDES REPRESENTING ANTIGENIC EPITOPES OF DOG IGE PRESENT ON B CELL BUT NOT BASOPHIL SURFACE

RELATED APPLICATIONS

This application is a continuation-in-part of Ser. No. 08/137,253, filed Oct. 14, 1993, which is a continuation-in-part of Ser. No. 08/090,527, filed Jul. 9, 1993 (U.S. Pat. No. 5,342,924), which is a continuation-in-part of Ser. No. 07/973,321, filed Oct. 29, 1992 (U.S. Pat. No. 5,254,671), which is a continuation-in-part of Ser. No. 07/515,604, filed Apr. 27, 1990 (U.S. Pat. No. 5,274,075), which is a continuation-in-part of Ser. No. 07/468,766, filed Jan. 23, 1990 (U.S. Pat. No. 5,260,416), which is a continuation-in-part of Ser. No. 07/369,625, filed Jun. 21, 1989 (abandoned), which is a continuation-in-part of Ser. No. 07/272,243, filed Nov. 16, 1988 (U.S. Pat. No. 5,091,313), which is a continuation-in-part of Ser. No. 07/229,178, filed Aug. 5, 1988 (abandoned), which is a continuation-in-part of Ser. No. 07/226,421, filed Jul. 29, 1988, which is a continuation-in-part of Ser. No. 07/140,036, filed Dec. 31, 1987 (abandoned).

BACKGROUND

The immediate-type hypersensitivities, such as extrinsic asthma, hay fever, and allergic responses to certain food or drugs, are mediated primarily by immunoglobulin E (IgE). In an IgE-mediated allergic response, the allergen binds to IgE on the surface of mast cells and basophilic leukocytes (basophils). This binding causes a crosslinking of the IgE molecules and hence, the underlying receptors for the Fc portion of IgE (FcεR), and thereby triggers the release of pharmacologic mediators, such as histamine, the slow-reacting substance of anaphylaxis, and serotonin. The release of these mast cell and basophil products causes the various pathological manifestations of allergy.

IgE is produced by a particular class of B lymphocytes (B cells), which also bear IgE on their surface. If sensitized to specific allergens, the allergenspecific IgE is produced by B cells continuously.

IgE binds to the receptors for the Fc of IgE (FcεR) on the surface of basophils and mast cells very strongly. The association constant, Ka, is in the neighborhood of $1 \times 10^{10}$ liter/mole and the "off" time is more than 20 hour. The very strong and stable association of IgE with FcεR means that IgE is virtually always present on these cells. An immunotherapeutic agent targeting the IgE on B cells must not react with the IgE on basophils and mast cells. Antibodies which react with the IgE isotype will cross-link IgE and the underlying FcεR on basophils and mast cells and, when administered in vivo, will induce systemic release of pharmacologic mediators, leading to allergic symptoms and possibly anaphylaxis.

The development of monoclonal antibodies that recognize an antigenic epitope present on the IgE on B cells, but not the IgE on basophils, was described in U.S. Pat. No. 5,091,313. The method of using such antibodies for assaying for IgE-bearing B cells and for treating type I hypersensitivities is described therein. These antibodies can cause the pharmacological mechanism of antibody-dependent cellular cytotoxicity (ADCC) or complement mediated cytolysis, and thereby down-regulate or lyse IgE-producing B cells and thereby reduce or eliminate IgE. These mechanisms will not induce histamine release from the basophils and mast cells.

If a vaccine was developed which induced production of antibodies which could specifically target IgE-bearing B cells, without targeting any other cells, such a vaccine would be useful in treating allergy and related hypersensitivities. It has been observed that IgE is not needed for normal health, except perhaps for combatting parasites. Thus, depleting all IgE-bearing B cells would not produce any adverse effects.

Dogs are succeptible to a variety of allergies, among the more common forms being tick allergy and flea allergy dermatitis. The latter can be a serious problem in some dogs, as the allergic regions itch and dogs which scratch excessively produce bleeding open sores. The sores are uncomfortable for the afflicted dogs and can become infected.

SUMMARY OF THE INVENTION

The invention relates to antigenic epitopes (and peptides representing these epitopes) which are present on dog B cell membrane-bound immunoglobulins but not on the secreted, soluble form of the immunoglobulin. The invention also pertains to methods of exploiting these newly discovered epitopes for therapeutic and diagnostic purposes.

B cells express on their surface antibody molecules, which serve as receptors for antigens during immunological induction. The membrane-bound immunoglobulins differ from the secretory, soluble immunoglobulins synthesized by the same cells in that they have an extra peptidic piece that anchors them onto the B cell surface.

All membrane-bound immunoglobulins on B cells from different species for which amino acid sequences have been determined, have extra isotype-specific regions that anchor the immunoglobulins to the membrane. These peptidic regions have lengths ranging from 41 to 72 amino acids, and can be divided into three segments in terms of locations in relation to the plasma membrane. The middle segments of 25 hydrophobic and uncharged amino acid residues are in the membrane lipid bilayer. The C terminal hydrophilic segments of 3–28 amino acid residues are intracellular. The segments toward N-terminus contain 13 to 27 amino acid residues and are highly acidic and hydrophilic. They are located on the extracellular surface of the plasma membrane.

The length and the hydrophilic and highly charged nature of the extracellular segments indicates that this segment is exposed and accessible to antibodies. These antigenic epitopes located on the extracellular segment of membrane-bound region of immunoglobulin heavy chains can be generally designated mb/ec, and the mb/ec segment of ε immunoglobulin is designated as the ε.mb/ec segment.

The present invention pertains to the discovery of these ε.mb/ec epitopes and peptides representing them for dogs, and the use of such dog peptides and related and derivative immunogenic products for dog allergy treatment. These dog peptides and related and derivative immunogenic products can also be used for generating monoclonal and polyclonal antibodies which target the ε.mb/ec epitopes on B cells.

DETAILED DESCRIPTION OF THE INVENTION

1. Unique Antigenic Epitopes of IgE as Targets of Immunotherapeutic Agents

IgE is present on three cell types in the body: IgE-producing B cells, mast cells, and basophils. If an antigenic epitope of IgE is present on B cells and not on basophils and mast cells, these epitopes (defined as ige.bl) are virtually unique cell surface markers of IgE-bearing B cells and antibodies against them do not induce histamine release. These markers, therefore, provide targets for several types of monoclonal or polyclonal antibody-based therapy for IgE-mediated allergic diseases, and provide a means to differentiate B cells producing IgE from B cells producing other isotypes.

2. Anchoring Peptidic Piece of B Cell Membrane-bound Immunoglobulins The amino acid sequence of the ten membrane-bound immunoglobulins from several species have been determined. The amino acid sequence of the human ε.mb/ec segment has also been determined. U.S. Pat. No. 5,342,924. Comparison of all these sequences indicate certain common features of the plasma membrane-bound peptidic piece. The peptidic anchor piece has three segments which are distinguishable based upon their locations in relation to the plasma membrane. Even though these peptidic pieces are short, ranging from 41 to 72 amino acid residues, and have often been referred to as the "membrane-bound domain" the peptides are not entirely in the membrane lipid bilayer. In fact, only 25 amino acid residues (which are the largely hydrophobic residues and threonine and serine) located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains ($CH_3$ or $CH_4$) are very hydrophilic and are on the extracellular side of the plasma membrane. These N-terminus segments are the mb/ec segments.

The mb/ec segments of all immunoglobulins contain high proportions of charged amino acid residues, and are almost entirely acidic residues. Studies of the evolution of immunoglobulin heavy chains indicate the ε and γ chains are more related to each other (had more recent common ancestry) than to other chains (Lin, L. C. and Putnam, F. W., *Proc. Natl. Acad. Sci. USA*, 1981). In addition, the heavy chains evolved before the various mammals species, such as mice, rats, and humans, evolved. Thus, among the ten mb/ec segments that have been determined, it can be postulated that the murine, human, and rat ε.mb/ec will all be related to the dog ε.mb/ec. This indicates strongly that probes based on human ε.mb/ec can be used to find the ε.mb/ec exons of the dog genome or cDNA. The murine or rat ε.mb/ec segment has 19 amino acid residues, among them 8 Glu and 2 Asp residues, while the short isoform of the human ε.mb/ec has 15 amino acid residues.

3. Determining the Amino Acid Sequence of the Human ε.mb/ec Segment.

As described in priority application Ser. No. 07/369,625, filed Jun. 21, 1989 (abandoned), a number of well established procedures can be applied to determine the DNA sequence corresponding to the human ε.mb/ec segment. In one approach, where one screens the human genomic library, two different DNA probes (designated probe a and probe c in the priority applications) are used. DNA probe a, which is a 1.1 kb long cDNA derived from U266, a human IgE-producing cell line, and which covers most of length of human ε mRNA and represents the constant region of immnoglobulin ε.

The design of a probe c is based on the finding that the transmembrane segment of the membrane-bound domain (mb/tm segment) is very conserved among all the immunoglobulin genes so far sequenced. There is a segment of peptide and its corresponding coding DNA within this mb/tm segment that is nearly identical among all immunoglobulins. Probe c is a concensus sequence of various isotypes (IgG, IgE, IgM and IgD) from mouse, rat, rabbit and humans representing this mb/tm segment. The location of probes a and c in schematic form is shown in U.S. Pat. No. 5,091,313.

The human genomic DNA library is readily available. A preferred source is the library constructed using human lung fibroblast WI38 cells provided by Stratagene (La Jolla, Calif.). The genes are in λ vector and the inserted DNA have average sizes of 15K bp. Identification of the clones can be achieved by hybridization with the U266 cDNA probe a. The location of the gene segment corresponding to the membrane-bound region can be determined by using probe c. The sequence of the membrane-bound segment is then determined. The sequence of the short isoform is shown in U.S. Pat. No. 5,091,313, and that of the long isoform is shown in U.S. Pat. No. 5,254,671.

The assignment of the exons was made by identifying the nucleotides for splicing donors and acceptors, and by comparing them to the published homologous sequences of mouse membrane-bound ε chain, as well as to immunoglobulins of other classes. Two exons were found to exist.

4. Sequencing the Dog ε.mb/ec Segment.

In a method which was closely analogous to that described above for sequencing the human ε.mb/ec segment starting from the human genomic library (which is also described in priority application Ser. No. 07/369,625), a dog genomic library was screened. Radioactive human IgE cDNA probes covering the membrane and constant regions were used in the initial library screening. A phage clone was selected as a positive and the phage DNA was purified. On restriction digestion and Southern hybridization analyses, a Bam HI fragment (size ~2.6 Kb) was identified by using a radioactive human membrane IgE cDNA probe, representing the region of human IgE designated m0-m2 in U.S. Pat. No. 5,274,075. A much larger (7.5–8 Kb) XhoI fragment lit up with the probe coding for the CH2–CH3 region of mouse ε chain. The BamHI fragment was found to be part of the larger XhoI fragment. Hence, the XhoI fragment was predicted to contain both the constant and membrane regions.

Further characterization of the DNA was simplified by subcloning and restriction enzyme mapping the above fragments into known plasmid vectors, and then sequencing them via the Sanger dideoxy method, using $^{32}P$ or $^{35}S$ labeled nucleotides. This enabled the identification of the membrane IgE region (SEQ ID NO:2), which was confirmed by comparing with the known mouse membrane sequence. The extracellular membrane-bound domain (based on a plot of hydrophobicity/hydrophilicity) is the first 19 amino acid residues shown in SEQ ID NO:2. This region is fairly hydrophobic, and abuts a hydrophilic region. Using a similar approach, the constant region was identified. This was compared to the chimpanzee IgE constant region sequence for confirmation.

5. Producing a Cell Line which Secretes Dog IgE.

A chimeric heavy chain vector was next constructed using the heavy chain variable gene of BAT123 (an anti-HIV-1 mouse monoclonal antibody which is described in pending U.S. application Ser. No. 07/950,571, and in WO 88/09181) and the 7.5 Kb XhoI genomic fragment, (containing the $CH_1$, $CH_2$, $CH_3$, $CH_4$, $M_1$ and $M_2$ region of Dog IgE and a 3' untranslated region), as the constant chain region. This vector was co-transfected along with the BAT123 mouse/human chimeric κ (which is described in pending application Ser. No. 07/898,383, and in WO 88/09181) light chain vector into NSO cells. Using 50 μg supercoiled DNA of the heavy chain and 10/ μg linear DNA of the light chain, $32 \times 10^6$ cells were transfected. The $11 \times 10^6$ viable cells recovered were plated out in 96 well plates at a density of one million cells per plate. These were screened using solid phase anti-hκ and HRP conjugated AB19-4 (which is an anti-idiotype antibody described in pending U.S. application Ser. No. 08/026,631 and in PCT/US90/07535).

Thirty-seven wells out of the 11 plates showed cell outgrowth. Twenty wells of out 37 showed an O.D. reading>0.05 by the screening procedure outlined above. After the MTT assay, cell lines DE1 and DE10 were generated which showed secreted Ig levels of 2 μg/$10^6$ cells in 24 hours. Expansion of DE1 was carried out in T-100 medium. Purification of 200 ml of supernatant, using an AB19-4 affinity column, yielded 700 μg of purified immunoglobulin. A reducing SDS-PAGE gel showed a light chain band identical to SE44 IgE and a slightly larger heavy chain band, confirming the presence of a secreted immunoglobulin with a BAT123 light chain. One liter and 3 liter spinner flasks were begun in T-100 medium, and 3.8 liters of supernatant was quantified by ELISA, and then prepared for purification.

6. Using the Dog ε.mb/ec Peptides as Immunogens

The purified material could be used as immunogens to generate monoclonal or polyclonal antibodies against dog IgE, using the techniques described below. Alternatively, the dog ε.mb/ec peptides, or portions thereof or longer peptides including such dog ε.mb/ec peptides, can be used in dogs as vaccines.

The dog ε.mb/ec peptide is predicted to be alpha-helical in structure, based on its amino acid sequence. Such an alpha-helical structure can be held in such conformation by several methods, including linking a so-called "leucine zipper" at both the N-terminal and/or the C-terminal ends. The leucine zipper is a repeating hepta-peptide in which "a" designates its N-terminal peptide and "g" designates its C-terminal peptide. In this repeating hepta-peptide, each "a" and "d" are hydropobic isoleucine or leuine residues. There are two dog ε.mb/ec peptide chains intertwined in the native alpha helix, and two chains are also preferred in the vaccine immunogen. The zipper formation(s) canm be used to hold both chains in the alpha-helical structure.

As an alternative to having the zipper at either end of the dog ε.mb/ec peptide chains, one could use it at only one end, and one could chemically link the opposite end to hold it in conformation. Preferably, the chemical linker would be at the N-terminus, and the zipper would be at the C-terminus. One could also use only one (and not two) of the dog ε.mb/ec peptide chains, and hold it in the alpha-helical conformation by other means. Or it may not be necessary to hold it in an alpha-helical conformation at all. A lone chain, or two parallell chains, or portions or extended peptides based on either, may function adequately as vaccines.

Another alternative is to use any of the dog peptides or immunogens described above in combination with one or more protein carries. Preferred protein carriers are keyhole limpet hemocyanin (KLH) or Bacillus Calmette-Guerin (BCG). Recombinant protein antigens from rabies virus or from feline leukemia virus can also be used. These carriers can be conjugated to the peptides or immunogens, or the entire carrier-peptide can be expressed from a recombinant host cell.

7. Developing Antibodies to the ε.mb/ec Segment.

As described more fully below, the dog ε.mb/ec peptides, and immunogens based on or derived from such peptides such as those described above in section 6, can be used to elicit antibodies which react specifically with membrane-bound immunoglobulin ε. These antibodies may be useful as products for diagnosing or treating type I hypersensitivities.

For this purpose, the peptides can be chemically synthesized by standard techniques of protein synthesis. A preferred method for synthesizing the peptides is with the RAMPS system (Du Pont, Wilmington, Del.), which applies Fmoc chemistry. Alternatively, the proteins can be biosynthesized by employing oligodeoxynucleotides encoding the peptides.

Peptides comprising the dog ε.mb/ec segment and connecting amino acids in the $CH_4$ domain can also be used as immunogens. In addition, modified peptides having substantial immunological equivalency can be used. For example, the peptide amino acid sequence described below for dogs can be modified by deletion, insertion or substitution of one or more amino acids which do not essentially detract from the immunological properties of the peptide. The peptides can also be used as polymers where the amino acid sequence shown above, or equivalent sequence, is the polymer repeat unit.

The dog ε.mb/ec peptides and immunogens can be used in the immunization of animals to prepare polyclonal and monoclonal antibodies. They can also be used to screen for specific monoclonal antibodies or characterize specific polyclonal antibodies. They can also be used to purify monoclonal and polyclonal antibodies.

In the process of preparing for monoclonal antibodies specific for dog ε.mb/ec peptide, it is not necessary to use the dog ε.mb/ec peptide in both immunization and antibody identification. For example, in immunizing mice for preparing immune spleen cells for fusion with myeloma cells, the immunogen may be the membrane-bound IgE isolated from plasma membrane of IgE-bearing myeloma cells. The immunogen may also be the IgE-bearing myeloma cells themselves. The immunogen can also be the purified dog IgE described above.

For using the synthetic dog ε.mb/ec peptide as the immunogen, it is more effective to conjugate the peptide to a protein carrier. Preferred protein carriers are KLH or BCG, but one can also use recombinant protein antigens from rabies virus or from feline leukemia virus. If the dog peptidic segment used lacks a lysine residue or if the lysine residue is in the middle part of the segment, it is desirable to add a lysine residue at the C-terminal end. Because the N-terminus already has an α-amino group, the modified synthetic peptidic will have two amino groups available for linking to the carrier.

Multiple molecules of peptides can be conjugated to each molecule of the carrier protein. With KLH, a preferred molar ratio for peptide/KLH is 10. The method of conjugation is very well established. Cross-linkers such as glutaraldehyde or bis (sulfosuccinimidyl) suberate or disulfosuccinimidyl tartarate (Catalogue #21579, 20591, Pierce Chemical Co., Rockford, Ill.) have been used. A preferred cross-linker is the latter.

The immunogen, such as the KLH conjugate, can be used to immunize rabbits, goats, rats, or mice to prepare polyclonal antibodies specific for the ε.mb/ec peptide. Lympocytes from the spleen or lymph nodes of immune mice and rats can also be taken to prepare hybridomas secreting monoclonal antibodies specific for the ε.mb/ec peptide. A preferred protocol to prepare the monoclonal antibodies is to fuse immune spleen cells of mice with non-secreting mouse myeloma cells, such as NS-1 or SP2/0 cells using polyethylene glycol.

In one immunization protocol for mice, 50 μg of the peptide-KLH conjugate in complete Fruend's adjuvant is injected subcutaneously into each mouse for priming. Two and four weeks later, the same amounts of antigen are given s.c. in incomplete Freund's adjuvant. At about the six week time point, the fourth antigen injection is given i.p. in saline. Mice are sacrificed 4 days after the last injection and the spleens are taken for preparing single cell suspension for fusion with myeloma cells. A similar protocol can also be used for immunization with purified native membrane-bound IgE (having attached membrane anchor domain) isolated from the plasma membrane of IgE-bearing myeloma cells. When IgE-bearing cells are used as the immunogen, $1\times10^7$ cells are injected i.p. at two week intervals.

The fusion procedure with polyethylene glycol and other various procedures concerning cloning and hybridoma culturing have been well established, and the preferred protocol is the same as described by Hudson, L. and Hay. F. C., (*Practical Immunology*, 2nd edition, pp. 303–313, Blackwell Publishing Co., Boston). The screening of hybridomas for monoclonal antibodies, or the identification of polyclonal antibodies or the identification of polyclonal antibodies reactive with dog ε.mb/ec peptide can be performed with enzyme linked immunosorbent assays (ELISAs), using the synthetic ε.mb/ec peptide as the solid phase antigen. An alternative solid phase antigen is the conjugate of ε.mb/ec peptide with a different carrier protein such as bovine serum albumin different from that used in the immunogen. Further characteristics of the monoclonal and polyclonal antibodies would be that they bind to an ε.mb/ec peptide, or to IgE-bearing B cells, but do not bind to soluble IgE, or to IgE on basophils or mast cells (as measured by a histamine release assay).

8. Using the ε.mb/ec Peptides for Animal Treatment

The peptides of the invention can be tested in animal model systems to determine if they are suitable for allergy treatment in dogs. Also, the peptides of the invention can be used to treat other animals which are afflicted with allergies or other immediate-type hypersensitivities. For example, the cat, horse, or other mammalian ε.mb/ec peptides can be used to treat allergies or hypersensitivities in these respective animals.

When used to treat animals, the ε.mb/ec peptides or immunogens described above in section 6, with or without the carriers described there, are administered to the animal in a suitable pharmaceutical vehicle. Sub-cutaneous or intra-muscular injection is preferred as a route of administration. The dosage of peptide administered can vary widely depending on the size of the animal, but should be sufficient to create an immunogenic response in the animal. This would generally be in the range of about 10–100 μg/kg of animal body weight. The optimal dosage range can readily be determined with minimal experimentation during the clinical trials.

10. Diagnostic Uses for the Antibodies of the Invention.

Antibodies against ε.mb/ec epitopes (described above in section 7, and made using the peptides or immunogens of section 6) can be used to identify and enumerate IgE-bearing lymphocytes in a fluid sample, such as serum. Thus, the various antibodies which target the ε.mb/ec epitope of a particular species can be used diagnostically in that species for such identification and enumeration of its IgE-bearing B lymphocytes.

For this purpose, antibodies can be used in standard assay formats for determining cell surface antigens. In general, the antibody is contacted with a sample of the leukocytes to be tested under conditions which allow the antibody to bind IgE-bearing cells in the sample. The cells are then examined for binding of antibody. This can be accomplished by conventional cell staining procedures. For example, a fluorescently labeled second antibody can be used to detect binding of the anti-IgE antibody.

Equivalents

The terms, expressions and examples herein are exemplary only and not limiting, and those skilled in the art will recognize, or be able to ascertain using no more than routine experimentation, many equivalents to the specific embodiments of the invention described herein. Such equivalents are intended to be encompassed by the following claims.

I claim:

1. A peptide having the sequence of the ε.mb/ec segment of a dog produced by a method comprising:

preparing the dog genomic library by transfecting it into phage and selecting a phage clone positive for DNA encoding membrane-bound ε immunoglobulin;

purifying the phage DNA;

restriction digesting and analyzing the digested DNA fragments to identify a fragment which includes DNA encoding the membrane-bound domains of ε immunoglobulin and some of the adjacent constant region;

subcloning and restriction enzyme mapping said fragment into vectors;

sequencing said fragment;

identifying the portion of said fragment coding for membrane ε immunoglobulin by comparison with a known membrane coding sequence;

identifying the portion of said fragment coding for the extracellular membrane-bound domain of dog ε immunoglobulin, based on a plot of the hydrophobicity/hydrophilicity of the amino acid sequence it codes for; and producing the ε.mb/ec peptide coded for by said portion and isolating said peptide.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 479 nucleotides
( B ) TYPE: nucleic acid
( C ) STRANDEDNESS: single
( D ) TOPOLOGY: linear ( x i ) SEQUENCE DESCRIPTION: SEQ ID NO:1:

```
AGGTGGCCTG CCACTCCAGC GCCAGCAGGG CTGCCGAGGC    40

CAGGGCATCA TTCTTGTGTC CCTCGGGGAG GGGGGGCGGG    80

TCTGCCTTCC CCCCACCAGC ACATGAAGCG GCTGGACCGG   120

GGAGGGCTGA CTGGCCGGTG CCCCCGC   147

GAG CTA GAG CTC CAG GAG CTG TGC GCG GAT GCC   180
Glu Leu Glu Leu Gln Glu Leu Cys Ala Asp Ala
              5                    10

ACT GAG AGT GAG GAG CTG GAC GAG CTG TGG GCC AGC CTG   219
Thr Glu Ser Glu Glu Leu Asp Glu Leu Trp Ala Ser Leu
            15                  20

CTC ATC TTC ATC ACC CTC TTC CTG CTC AGC GTG AGC TAC   258
```

```
Leu  Ile  Phe  Ile  Thr  Leu  Phe  Leu  Leu  Ser  Val  Ser  Try
25                       30                       35

GGC  GCC  ACC  AGC  ACC  CTC  TTC  AAG                       282
Gly  Ala  Thr  Ser  Thr  Leu  Phe  Lys
          40                       45

GTGGGCATGC  AGAGCCCTG  TGCCGGGGGT  GGGGGCAGCA                322

CAGAGGGAGG  GAGAGGTCCC  GGCAGAGCTA  TCCTCACATG               362

TGCCCTCCCC  CCAG                                             376

GTG  AAG  TGG  GTA  CTC  GCC  ACC  GTC  CTG  CAG  GAG  AAG  CCA  415
Val  Lys  Trp  Val  Leu  Ala  Thr  Val  Leu  Gln  Glu  Lys  Pro
               50                       55

CAG  GCC  GCC  CAA  GAC  TAC  GCC  AAC  ATC  GTG  CGG  CCG  GCA  454
Gln  Ala  Ala  Gln  Asp  Tyr  Ala  Asn  Ile  Val  Arg  Pro  Ala
          60                  65                       70

CAG  TAGGCCCAGA  GACACGGTGA  CG                              479
Gln
```